United States Patent [19]

Halley et al.

[11] Patent Number: 4,969,351
[45] Date of Patent: Nov. 13, 1990

[54] APPARATUS FOR DETERMINING DRAINAGE TIME OF PAPERMAKING STOCK

[75] Inventors: David G. Halley, Renton; Jerome M. Gess, Bellevue, both of Wash.

[73] Assignee: Weyerhaeuser Company, Tacoma, Wash.

[21] Appl. No.: 421,916

[22] Filed: Oct. 16, 1989

[51] Int. Cl.$^5$ ............................................. G01N 33/34
[52] U.S. Cl. ......................................................... 73/63
[58] Field of Search ...................... 73/63, 61.4; 162/49, 162/198, 258, 263

[56] References Cited

U.S. PATENT DOCUMENTS

| | | |
|---|---|---|
| 2,602,325 | 7/1952 | Campbell et al. ........................ 73/63 |
| 2,734,378 | 2/1956 | Meyers ..................................... 73/63 |
| 4,024,754 | 5/1977 | Alfthan .................................... 73/63 |
| 4,613,406 | 9/1986 | Gess .................................... 73/63 X |
| 4,708,011 | 11/1987 | Rautakorpi et al. ..................... 73/63 |

Primary Examiner—Hezron E. Williams
Assistant Examiner—Joseph W. Roskos

[57] ABSTRACT

The invention is an apparatus and method for measuring drainage time of a papermaking stock suspension. The apparatus will automatically measure drainage times of a plurality of samples which will preferably be of differing basis weights. It consists of a sheet mold reservoir and dropleg which index against or away from a table having spaced apart sheet forming locations. Operation of the apparatus is determined by a programmable controller which causes stock to be automatically transferred to the sheet mold and the reservoir and dropleg to be automatically and appropriately positioned. After a sheet is formed the table automatically indexes to the next forming position where the cycle is repeated. The method involves plotting a series of at least three points to determine the slope of drainage time versus the basis weight of the sheets formed. This can be used as an indicator of the drainage characteristics of a stock of given basis weight on the forming section of a paper machine.

14 Claims, 7 Drawing Sheets

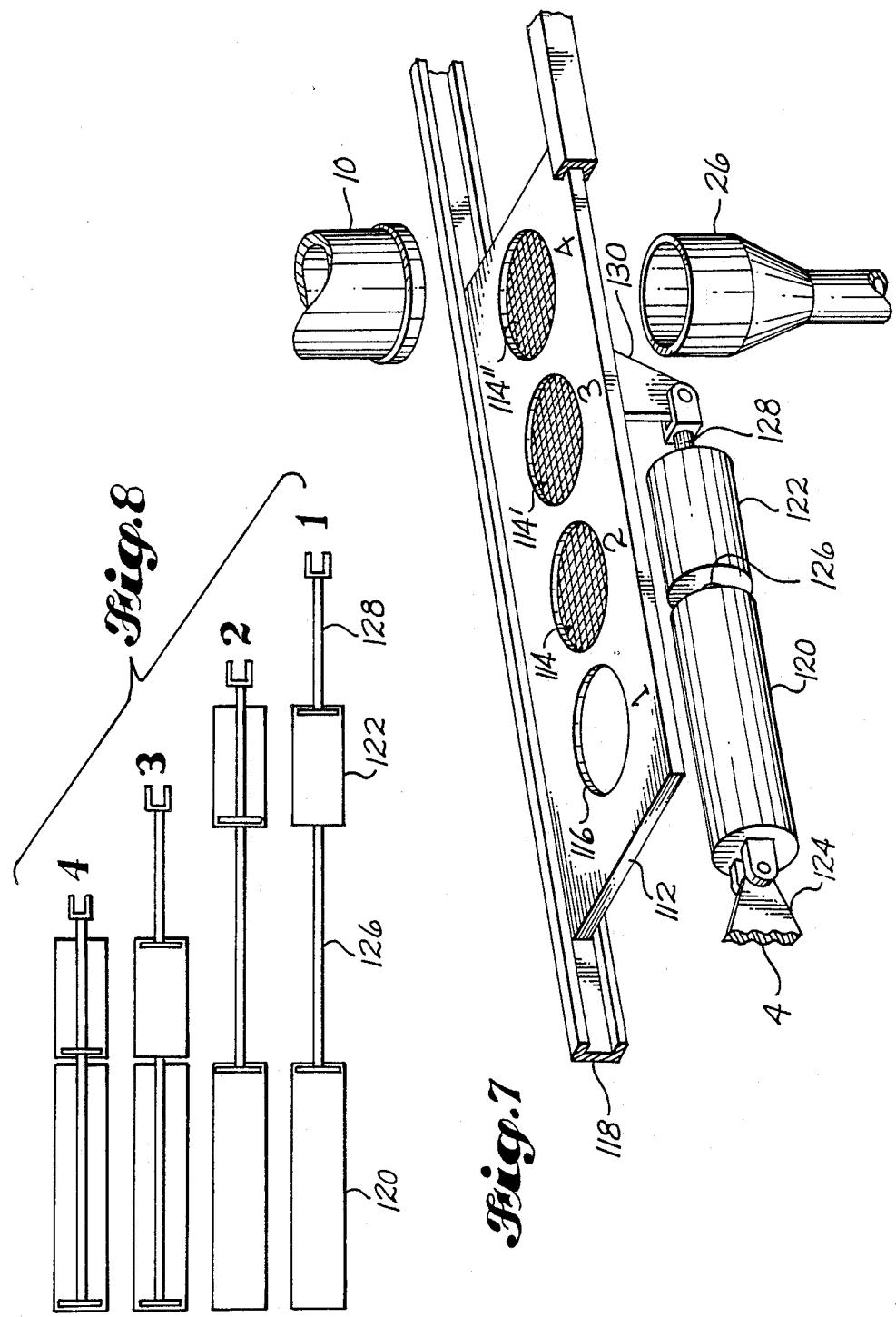

APPARATUS FOR DETERMINING DRAINAGE TIME OF PAPERMAKING STOCK

BACKGROUND OF THE INVENTION

The present invention comprises apparatus for measuring the drainage time of a papermaking stock suspension in a manner that can accurately predict the performance of the stock on the forming section at the wed end of a paper machine.

Paper makers have long had available a choice of simple methods and apparatus for estimating drainage time of a given papermaking stock. One method (TAPPI Standard Drain Time) normally involves placing a standardized sample of the stock in a small laboratory sheet mold and visually estimating the time for sheet formation when a drain valve is opened. The values so obtained may or may not correlate well with the performance of the same stock at the paper machine wet end.

A more sophisticated way of measuring the drainage characteristics of a papermaking stock is given in U.S. Pat. No. 4,613,406 to Gess. In this patent a slurry is dewatered in a sheet mold using vacuum under the forming wire. The pressure differential across the sheet is measured as a function of time. When the data so obtained are plotted, the resulting curve shows four generally linear sections of different slopes. The inflection point between the first two linear curves is believed to note the transition point of a random collection of fibers forming a web as the stock is being dewatered. This inflection point is believed to correlate with the wet line on the forming section. The inflection point between the second and third linear sections indicates where there is no further compaction of the web from the forces resulting from the vacuum applied near the end of the forming section. This is believed to correspond closely to the dry line on a forming section. Finally, the inflection point between the third and fourth linear portions of the curve indicates where dewatering is essentially complete and air is first drawn through the web. The apparatus and method of its use is further described by the above inventor in the following publications: *Proceedings*, TAPPI Papermaking Conference, Portland, Oreg., pp. 185-189 (1983) and Notes, TAPPI Retention and Drainage Seminar, pp. 75-81 (1983).

The above author further describes the use of the above drainage time measurement apparatus in TAPPI, *Advanced Topics in West End Chemistry Short Course*, Memphis, Tenn. (1987). In this paper he additionally shows and describes a curve of sheet weight versus drainage time and discusses how this relates to fines sensitivity of the forming system. A curve having two linear portions of different slope results as the sheet weight is increased. This is further discussed by the same author in two more recent papers: TAPPI, *Retention and Drainage Short Course*, pp. 49-52 (1989) and *Preprints*, TAPPI Annual Meeting, pp. A27-A32 (1989).

The first linear portion of the plot of sheet weight versus drainage time indicates that forming wire geometry is of primary importance in the retention of fine particles. The second linear portion suggests that the sheet itself is acting as a filter medium for fines retention.

While the apparatus described in U.S. Pat. No. 4,613,406 has seen widespread use, it is basically a laboratory instrument rather than one which can be used in the hour-to-hour control of an operating paper machine. The present invention provides apparatus which can rapidly form a series of sheets of differing basis weight to give the wet end tender a timely indication of factors such as white water fines buildup that would affect operation of the forming section.

SUMMARY OF THE INVENTION

The present invention comprises apparatus for measuring the drainage time of a papermaking stock suspension. The values measured are useful for predicting performance of the stock on the forming section of a paper machine.

The apparatus comprises a number of associated elements. Among these are included a container for suspension of the papermaking stock and a sheet mold mechanism. The sheet mold mechanism comprises a movable table underlying the stock reservoir of a sheet mold. The table has a plurality of spaced apart sheet forming locations. An indexing mechanism for the table is used to position it from one sheet forming location to an adjacent sheet forming location. Beneath the table is a dropleg which is located generally axially below the sheet mold reservoir. The dropleg has a valve which may be closed, to enable the sheet mold to be filled, and opened to drain it. There is also a transfer means to deliver a predetermined amount of stock from the stock suspension container to the sheet mold reservoir.

In a preferred mode of construction a rotatable turntable having angularly space apart sheet forming locations is used. Alternatively, the table can have side-by-side sheet forming locations and be linearly indexed to the desired location.

The various elements are linked by a timing and control system which starts and regulates a set of predetermined sheet forming operations so that a plurality of sheets can be automatically and sequentially formed. Finally, a drainage time measurement sensor determines the stock drainage time.

The apparatus functions as follows: data including the desired sheet or pad weight and sample stock consistency are entered into a programmable controller in the timing and control system. Additionally, data are entered indicating whether sequential samples in the series should differ in sheet weight from the original sample and, if so, the madnitude of the difference or differences. At this time a signal is then given to the control system to begin the first sheet forming cycle.

While it is not a limitation of the apparatus, it is necessary in the process related to the invention to preferably form at least three sequential sheets which differ from each other in basis weight by some predetermined incremental amount. The drainage time of each sheet is then determined and a plot is made of drainage time versus basis weight. Using this plot the drainage time of a sheet having any basis weight within the range of the data can be easily predicted.

It is known that plots of increasing basis weight versus drainage time will have a first linear portion, then a transition zone, and then a second linear portion of differing slope from the first. The shape of this curve is believed to result from the following forces which are at work on the sheet as it is formed. The first linear portion is speculated to be caused under conditions in which the geometry of the forming wire or screen is controlling of fines retention. In the transition zone both the forming wire and the sheet itself affect fines retention. Finally, in the second linear portion, the filtering action of the sheet itself effects retention of fines and the wire geometry is of little or no consequence. It is preferred that all basis weight values in the series of tests run for the present method should be in either the frist or the second linear zones of the above curve.

It is an object of the present invention to provide an apparatus which will easily and automatically measure the drainage time of a plurality of papermaking stock samples in a manner that will relate to real time paper machine operations.

It is another object of the invention to provide apparatus that will automatically measure drainage time of a plurality of samples which differ by some predetermined increment in basis weight.

These and many other objects will become readily apparent upon reading the following detailed description taken in conjunction with the drawings.

BRIEF DESCRIPTION OF THE DRAWINGS

FIG. 7 is a perspective view of an alternative construction of the apparatus.

FIG. 8 shows a position control mechanism for the embodiment of FIG. 7.

DETAILED DESCRIPTION OF THE PREFERRED EMBODIMENTS

Figures 1, 4:
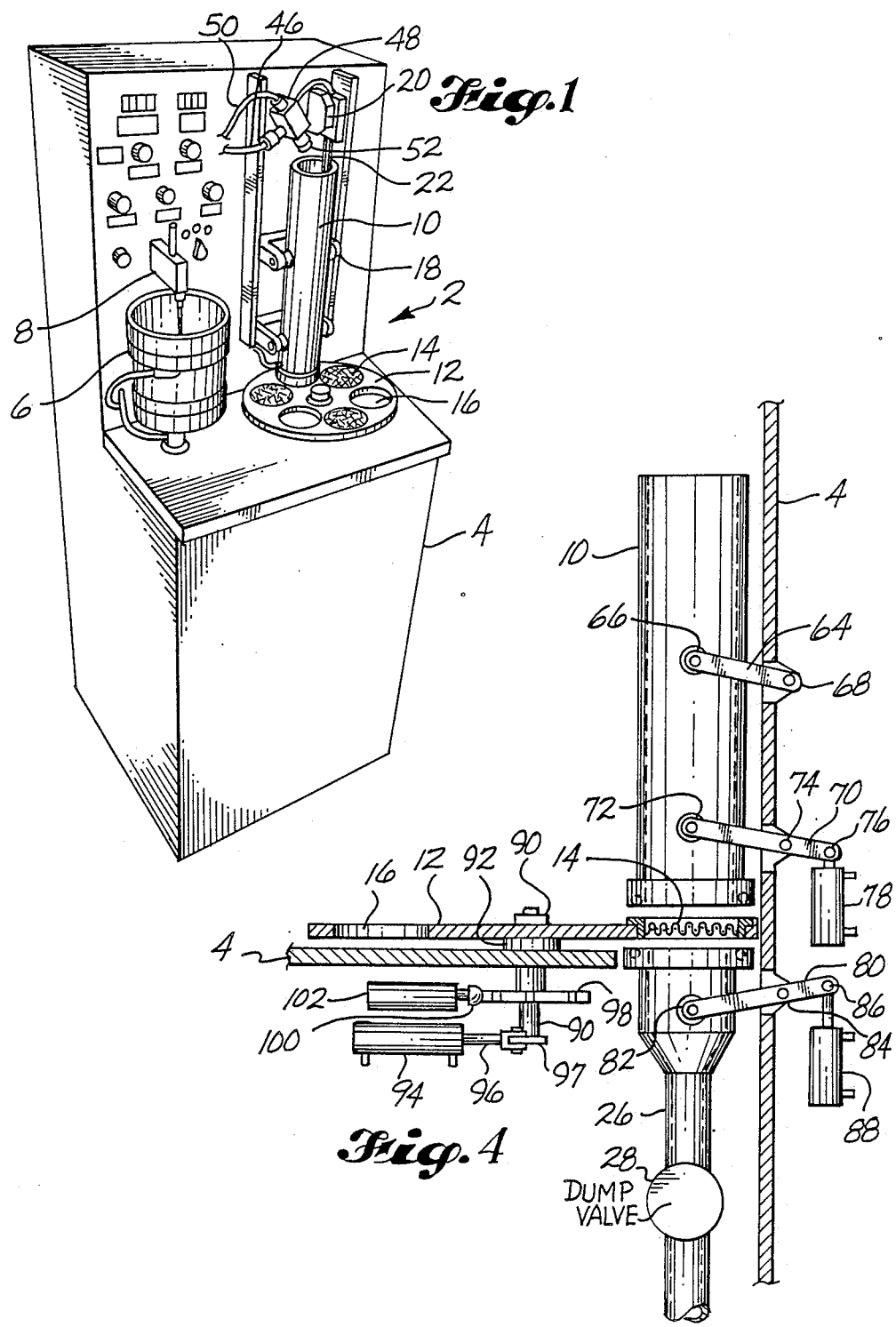
FIG. 1 is an overall perspective view of the drainage time test apparatus.
FIG. 4 is a side elevation, partially in cross section, of the sheet forming portion of the apparatus.

The construction and operation of the apparatus of the present invention, and the method of its use, can best be understood by reference to the drawings. One form of the apparatus is shown generally at 2. It consists of a cabinet 4 which houses various timing and control elements, not shown, and which provides structural mounting surfaces for other elements of the apparatus. Included among these elements is a container 6 for holding the papermaking stock being tested. This is kept in the form of a uniform aqueous suspension by an optional agitator 8 and circulating pumps 36 and 42. Adjacent the stock container is a sheet mold reservoir 10 having a lower end 11. The reservoir is indexed into or out of liquid tight contact with a turntable 12 having a number of sheet forming locations 14 which alternate with sheet mold reservoir rinsing locations 16. A positioning mechanism 18 determines when the sheet mold reservoir is in or out of contact with turntable 12.

Mounted above the sheet mold reservoir is a drainage time measurement device 20. This preferably consists of a light source and photocell to measure reflectance from the surface of the stock held within the sheet mold reservoir.

Figure 2:
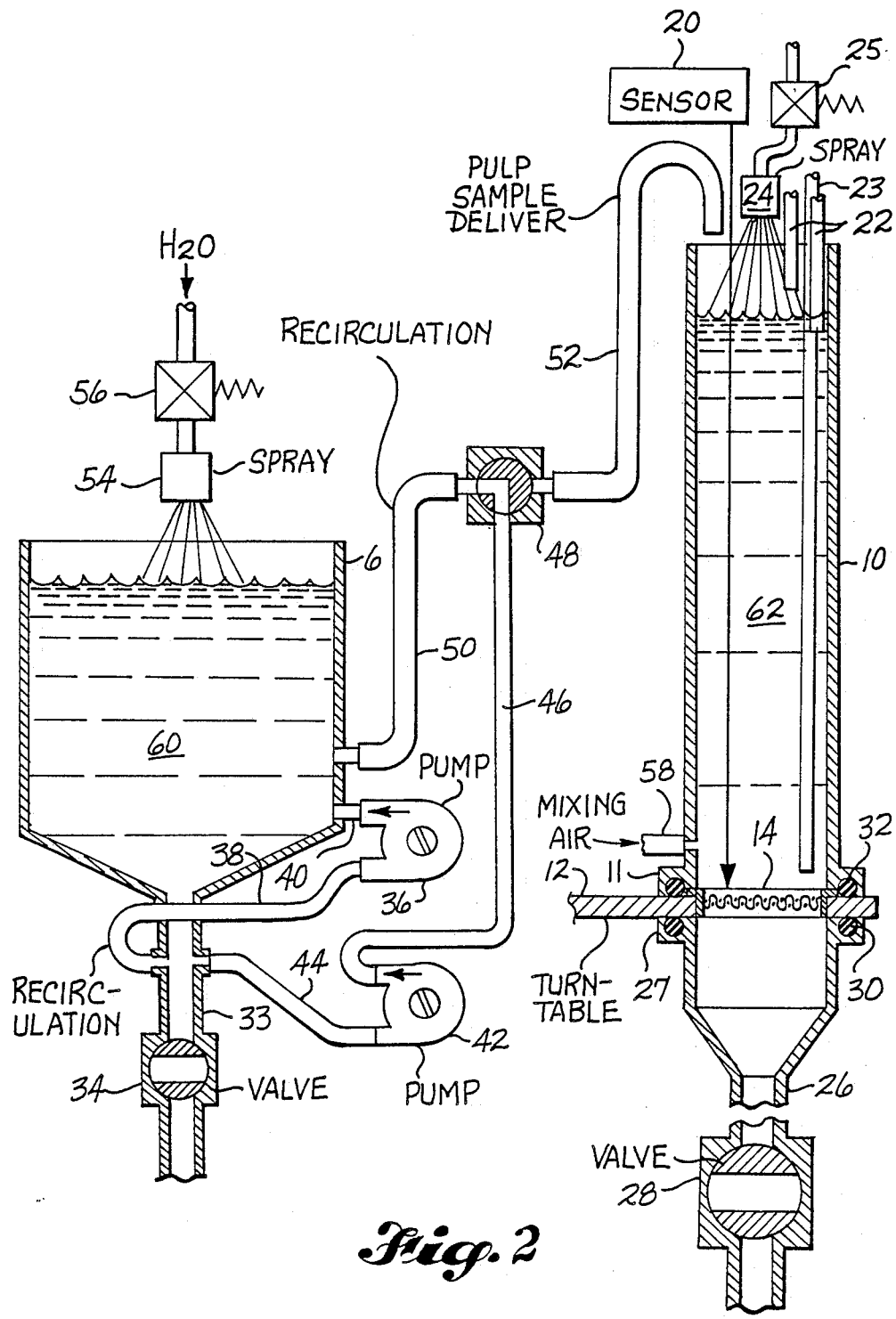
FIG. 2 is a simplified cross-sectional view of a portion of the apparatus just prior to sheet formation.
Figure 3:
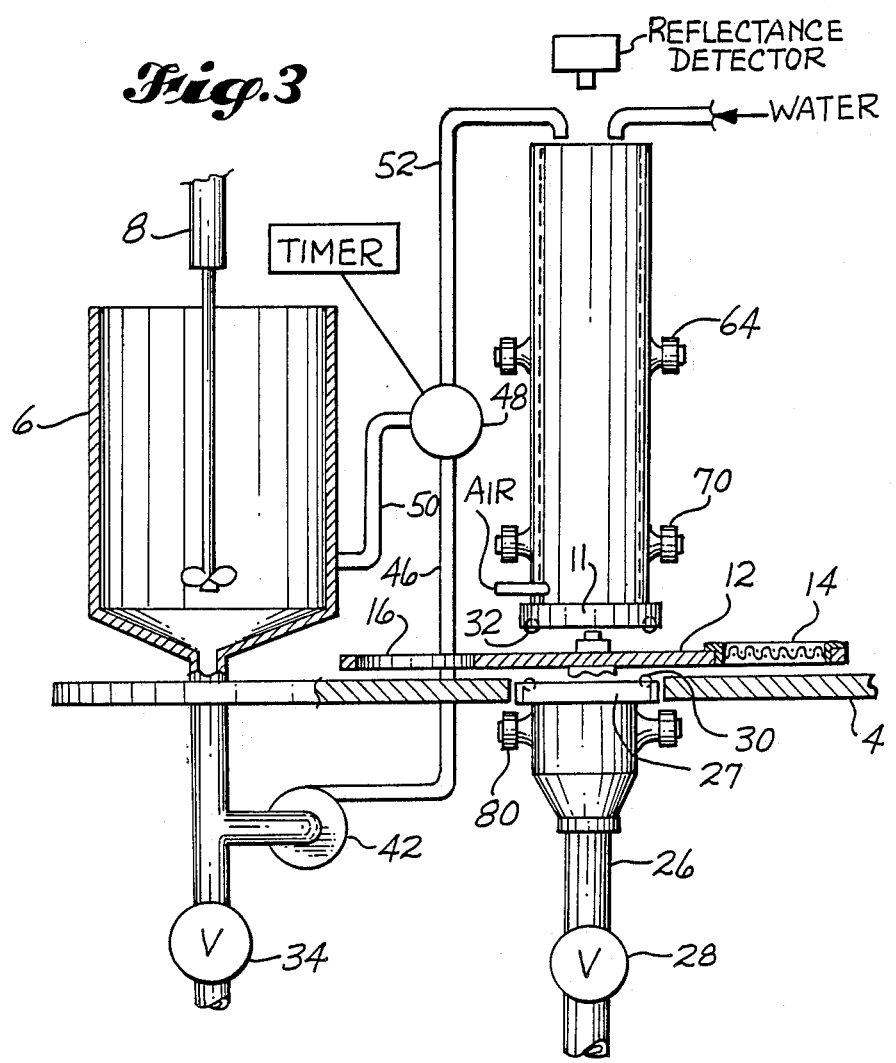
FIG. 3 is a simplified view, partly in cross section, of the apparatus at another stage of operation.

Referring for the moment to FIG. 2, a sample present sensor 23, a water spray nozzle 24 and a spray nozzle control valve 25 are also mounted above the sheet mold reservoir.

Still referring to FIG. 2, and also to FIG. 4, a dropleg 26 is mounted below turntable 12 in axial alignment with the sheet mold reservoir 10. The droplet has an upper portion 27 also adapted to engage the turntable in liquid tight contact. The lower portion of the dropleg has a valve 28 which when closed enables the sheet mold reservoir to be filled with water and papermaking stock and when open allows the stock to drain so as to form a sheet or pad on forming wire or screen 14. O-ring seals 30, 32 located respectively in the turntable contacting portions of the dropleg and sheet mold reservoir serve to maintain water tight integrity of these elements when in contact with turntable 12.

Figure 6:
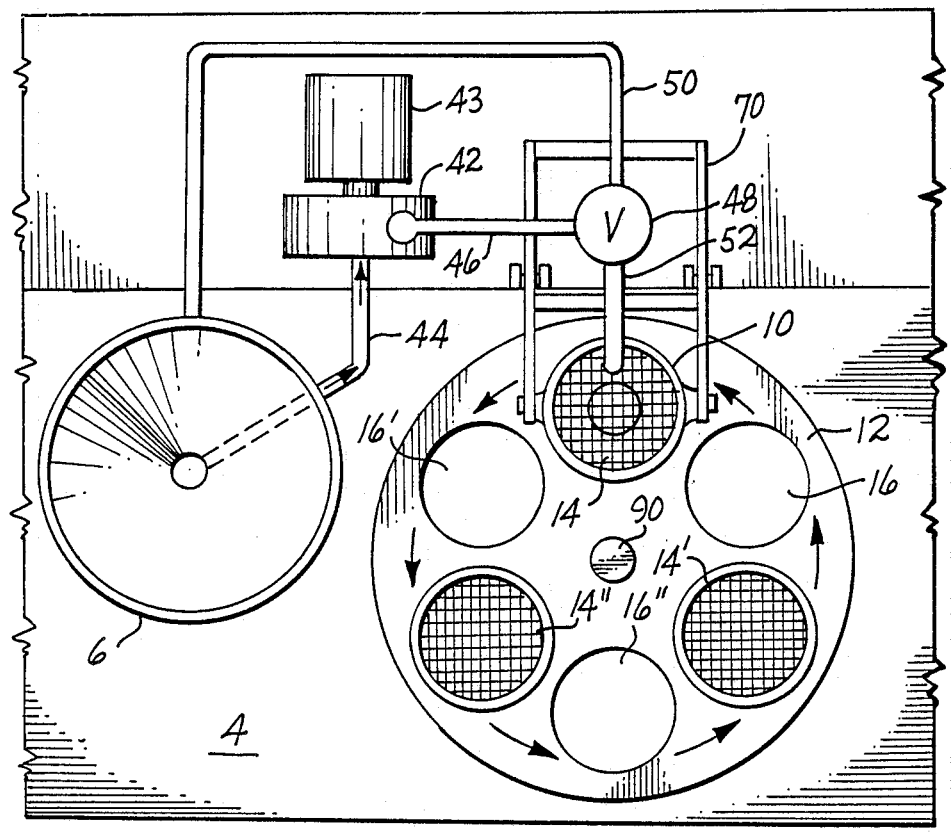
FIG. 6 is a top plan view including the turntable and other key portions of the apparatus.

Reference should now be made to FIGS. 2, 3, 4, and 6. Stock container 6 is seen to have a drain line 33 closed by a valve 34. A first recirculation pump 36 draws papermaking stock 60 from the lower portion of the stock container 6 through line 38 and returns it through discharge line 40 at a higher level in order to help maintain uniformity and prevent consistency variations within the sample being tested. A second pump 42, which serves both as a recirculation pump and a sample transfer pump, also draws stock 60 from the lower portion of container 6 through line 44. This is discharged through line 46 to a three way valve 48. The position of this valve determines whether stock is recirculated through line 50 to reservoir 6 or whether it is transferred through line 52 to the sheet mold reservoir. Recirculation/sample transfer pump 42 is driven by a motor 43 (FIG. 6). A water spray nozzle 54 is mounted above stock container 6 for thorough rinsing between different samples. Valve 56 controls the flow of water through spray nozzle 54.

Referring again to FIG. 2, in which the sheet mold reservoir and dropleg are in position against the table for sheet formation, sheet mold reservoir 10 is filled with and appropriate portion of papermaking stock 62 which for a given period of time prior to sheet formation is agitated by the addition of air bubbles through inlet line 58.

Looking now at FIG. 4, the sheet mold reservoir positioning mechanism 18 will now be further defined. The position of sheet mold reservoir 10 is controlled by the location of an upper parallelogram arm 64 which is pivotally attached to the sheet mold reservoir at 66 and to the cabinet at 68. A lower parallelogram arm 70 is pivotally attached to the sheet mold at 72 and to the cabinet at 74. A control cylinder 78 operates against one end of arm 70 to control the position of sheet mold reservoir 10 relative to turntable 12. In similar fashion, a dropleg position control arm 80 is pivotally attached to dropleg 26 at 82 and similarly attached to the cabinet at 84. A drop leg position control cylinder 88 is pivotally attached to arm 80 at its end 86.

Figure 5:
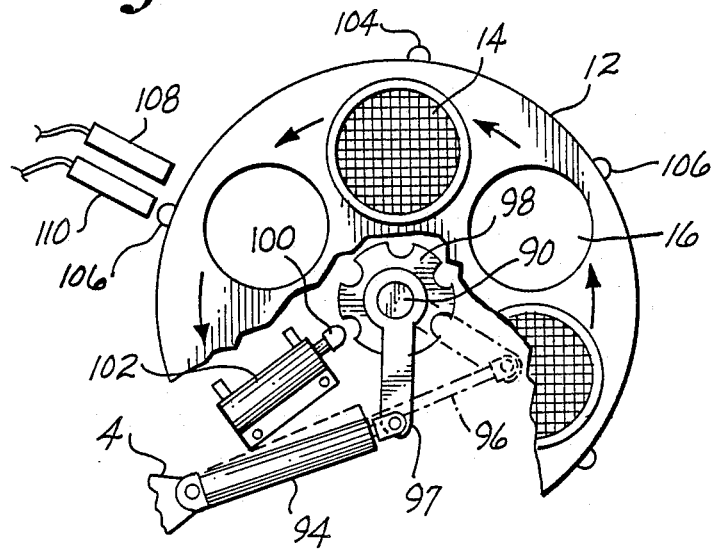
FIG. 5 is a top plan view, partially cut away, of the turntable indexing mechanism.

Reference can now be made to the turntable indexing mechanism shown in FIGS. 4 and 5. Turntable 12 is mounted on a shaft 90 which is journaled to cabinet 4 in a bearing 92. A position control cylinder 94 has a piston rod 96 pivotally attached to one end of a control arm 97. The other end of control arm 97 acts on shaft 90 through a ratchet mechanism (not shown). In this way, when piston rod 96 is extended, as is shown in phantom form on FIG. 5, the turntable is rotated step-wise one position. However, no rotation occurs when the piston rod is retracted due to the action of the ratchet mechanism. The turntable is precisely positioned at each location through the use of a detent plate 98 and a detent 100 which is extended or retracted by detent cylinder 102. Further, a sensing means is used to determine that the turntable is in precise position and send this information back to the timing and control means. This mechanism consists of a proximity sensor 108 located to sense screw heads 104 when the turntable is in a forming location. Additionally, proximity sensor 100 senses screw heads 106 when the turntable is in a rinsing location.

An alternative form of construction of the apparatus is shown in FIGS. 7 and 8. Here the turntable 12 is replaced with a linearly acting table 112. This has three sheet forming locations 114, 114', 114'' and a single rinse location 116. The table is slidably mounted in a pair of channels 118 which are in fixed position on cabinet 4. Position of the table is controlled by a pair of end-to-end fluid cylinders 120, 122. The fixed end of cylinder 120 is attached to cabinet 4 at 124. The piston rod 126 of cylinder 120 is attached to the fixed end of cylinder 122 whose piston rod 128 is, in turn, attached to arm 130 depending from table 112. Cylinder 120 is selected to have a stroke that is twice that of cylinder 122. The stroke of cylinder 122 is selected or adjusted to be exactly equal to the distance between adjacent sheet forming locations.

FIG. 8 details the operation of the cylinders for positioning the table to the desired sheet forming or rinse location. With the pistons of both cylinders fully retracted the table is in sheet forming location 114''. With both fully extended the table will be in rinse location 116. As shown here, the table 112 will be reciprocated between sheet forming positions and the single rinse location. While additional rinse locations could be provided between each sheet forming position, the arrangement shown is preferred because the length of the table can thereby be reduced. A position location means, such as screw heads 104, 106 and proximity sensors 108, 112 (FIG. 5) can be provided if desired.

Other positioning arrangements besides the one shown could be readily designed by those skilled in the art.

Figure 9:
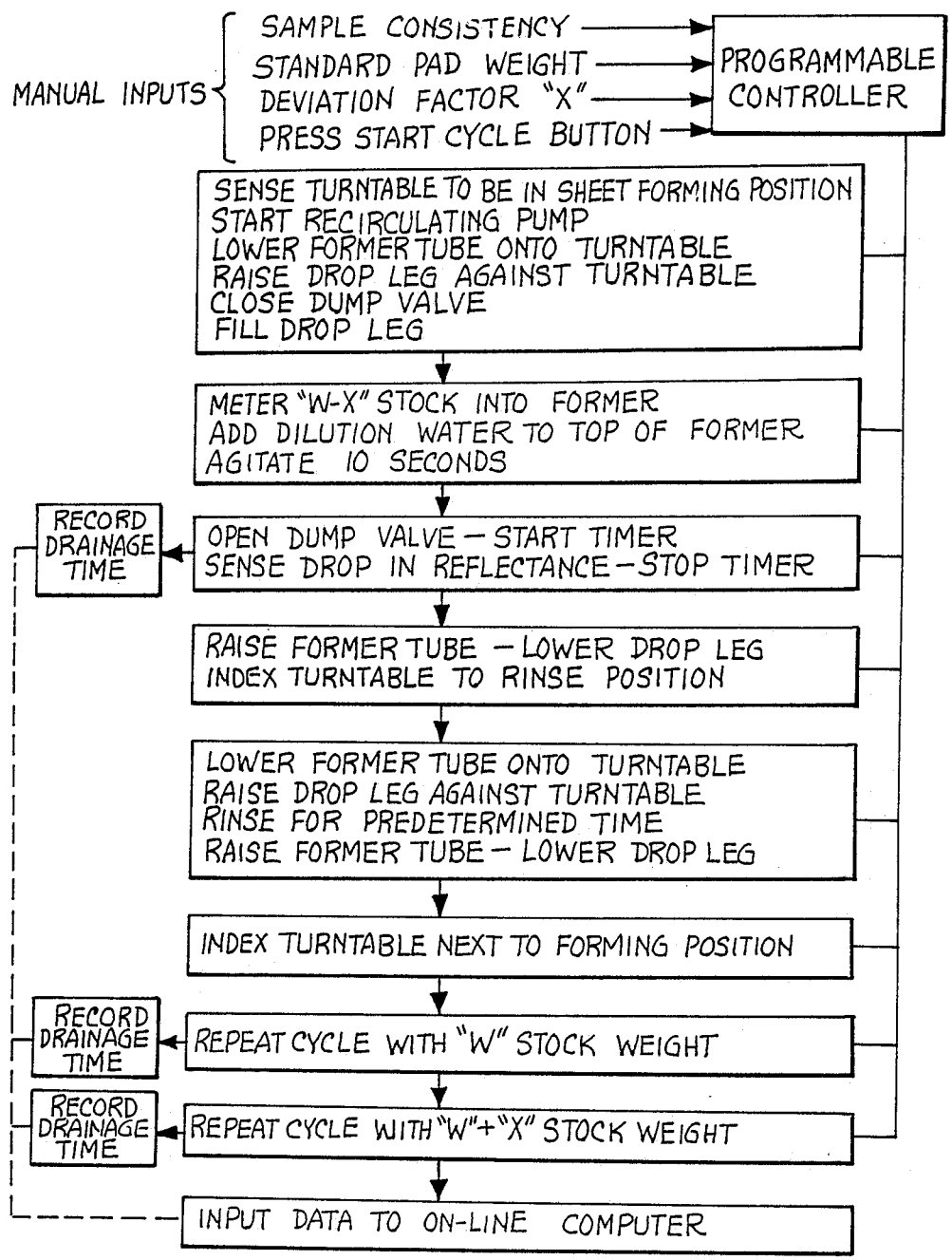
FIG. 9 is a block diagram indicating the various operating steps of the apparatus.

The operation of the apparatus will be now be explained. Reference can be conveniently made at this point to FIG. 9. The description here will be based on the apparatus shown in FIGS. 1-6. The necessary modifications for use of the apparatus of FIGS. 7 and 8 will be readily evident to one skilled in the art. Three manual inputs are normally made to the timing and control device which has as its heart a programmable controller. These inputs are sample consistency, a desired standard pad weight "W," and a deviation factor "X." The deviation factor will usually be some value within about 0 and 25% although it is not so limited. A more typical value is about 15%. With the three forming position apparatus described and the typical deviation factor, one sheet can be formed having the desired standard pad weight "W." A second one could be formed having a sheet weight 15% less or 0.85 W and the third sheet could be formed having a 15% greater weight or 1.15 W.

When the manual inputs have been entered, the operator presses a start cycle button. The timing and control apparatus then takes over and causes a number of operations to take place. First, it determines that a signal is being received from sensor 108 indicating that the turntable is in a proper sheet forming position. Then, the recirculating pumps are both started. At this time the sheet mold reservoir 10 is lowered into water tight position against the turntable and dropleg 26 is similarly raised. Dump valve 28 is closed and the dropleg is filled with water to at least the screen level.

In the next phase of operation, an appropriate portion of stock is metered into the sheet mold reservoir by pump 42 through three way sample valve 48. Dilution water is added through spray nozzle 24 and valve 25 until the water level has risen to an appropriate height as determined by sensors 22. While FIG. 9 indicates that the first sheet will have a basis weight of W-X, this is a matter of convenience only and the sheets may be formed in any order. It will be clear to those skilled in the art that the sheets may also be replicates of one another and need not differ in basis weight if it is desired to use the apparatus for purposes other than practicing the method of the invention. When the diluted stock in the sheet mold reservoir has reached the proper height, air is introduced through tube 58 for 10 seconds to ensure thorough mixing.

At this time the timing and control mechanism will cause the dump valve to open. This starts the timer. As the water level drops, the sheet is formed on the wire. Ultimately all of the water will have drained from the sheet mold reservoir and water moving down the dropleg will cause air to be drawn through the sheet. At this time there will be a sharp change in reflectance from the surface of the sheet which will be sensed by the drainage time detector and the timer will then be stopped.

As the next operation, the sheet mold reservoir will be raised and the dropleg will be lowered so that the turntable can be indexed to the rinse position. When proximity sensor 110 senses that the turntable is correctly positioned, the former tube will again be lowered and the dropleg raised into contact with the turntable. Then spray nozzle 24 and valve 25 will thoroughly wash the former tube. At this time dropleg dump valve 28 is in the open position. After the predetermined rising time, the former tube is again raised and the dropleg lowered. The turntable is then indexed to the next forming position. At this time the cycle is completely repeated using the appropriate weight of papermaking stock selected for the second cycle. As explained before, this will norminally be stock weight "W" but this is not essential.

Once again the cycle is repeated with the third stock weight selected.

Figure 10:
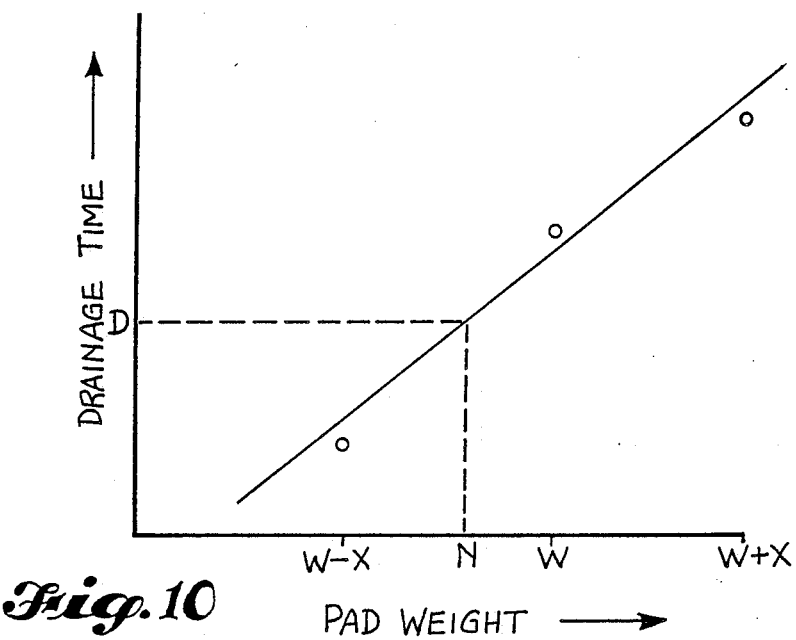
FIGS. 10 and 11 are plots of drainage time versus basis weight of the sheet for various papermaking stocks.

The operations just described above proceed fully automatically. After the final cycle in which the last sheet is formed, forming wires 14 are removed from the turntable, and the sheets stripped off and conventionally dried. Drainage times can be indicated as digitized output readings and they may also be entered directly into an on-line computer. When sheet weights are available, these, too, can be entered into the computer and the plot of pad weight versus drainage time given as an output. A plot of this type is seen in FIG. 10. With this plot the drainage time of any sheet having a basis weight "N" within the range of the data plotted can be readily determined.

Figure 11:
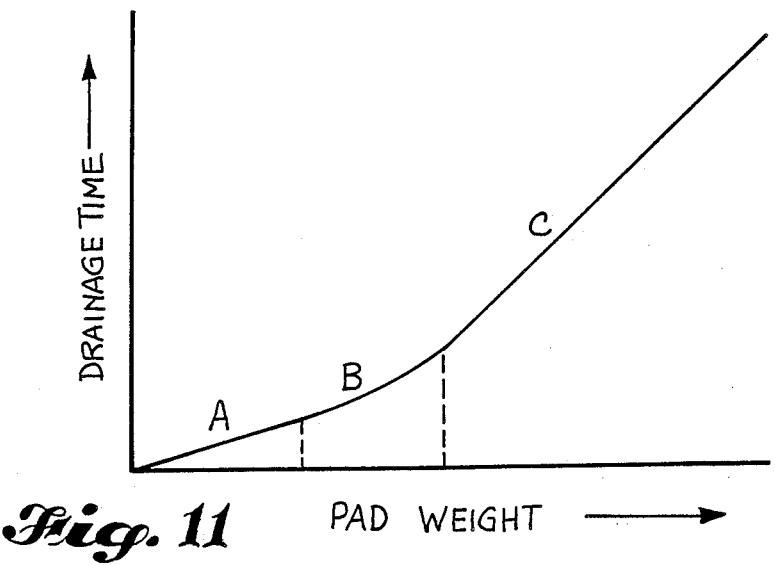

As noted before, the three basis weights "W," "W"-"X," and "W"+"X" will normally be within one of the linear ranges "A" or "C" as shown in FIG. 11. As previously explained, in linear range "A" the geometry of the forming wire is controlling while in linear range "C" the porosity of the cellulosic pad or sheet itself controls drainage time. The curve of FIG. 11 can be readily determined either using the present apparatus or any standard sheet mold well known in the art in order to establish operating parameters.

It will be evident from the preceding description that many variations can be made in the construction and operation of the apparatus. It will be understood that the scope of the invention is limited only as it is defined by the following claims.

We claim:

1. Apparatus for measuring the drainage time of a papermaking stock which comprises:
    a papermaking stock suspension container;
    a sheetmold reservoir means for holding a quantity of paper-making stock;
    a table means underlying said sheetmold reservoir means, said table means defining a plurality of spaced apart sheet forming locations;
    indexing means for said table means to position it from one sheet forming location to an adjacent sheet forming location;
    a dropleg underlying the table means, said dropleg being located generally axially below the sheetmold reservoir means;
    valve means to open and close said dropleg to enable filling and draining said sheet mold reservoir means;
    transfer means to deliver a predetermined amount of stock suspension from the stock suspension container to the sheetmold reservoir means;
    timing and control means for initiating and controlling a set of predetermined sheet forming operations whereby a plurality of sheets can be automatically and sequentially formed; and
    drainage time measurement means to measure stock drainage time,
    whereby when a start cycle signal is given, said timing and control means causes said sheet mold reservoir means to be positioned in a liquid tight relationship over a sheet forming location on the table means, then causes said transfer means to deliver the predetermined amount of stock suspension to the sheet mold reservoir means, then causes said reservoir means to be filled to a predetermined level with water, then causes the dropleg valve means to open to begin sheet formation and begin timer operation, then after said sheet has been formed and drainage time measured causes the indexing means to position the table means to the next sheet forming location so that said cycle may be repeated, said drainage time measurement means reporting drainage time for each cycle of the operation.

2. The apparatus of claim 1 in which said timing and control means is configured to cause sequential sheets to be of predetermined incrementally differing basis weights by controlling the amount of papermaking stock delivered by the transfer means.

3. The apparatus of claim 1 including means to position the sheetmold reservoir means and dropleg against a sheet forming location on the table means in liquid tight relationship during a sheet forming cycle and then move said sheetmold reservoir means and dropleg away from the table means after sheet formation to free said table means for indexing to the next sheet forming location.

4. The apparatus of claim 3 in which the sheet mold reservoir positioning means is a parallelogram arm mechanism.

5. The apparatus of claim 1 including an easily removable sheet forming wire means at each sheet forming location on the table means so that a formed sheet can be readily recovered.

6. The apparatus of claim 1 in which the drainage time measurement means is a surface reflectance measurement device located to sense the surface of the stock suspension in the sheet mold reservoir means at the beginning and end of sheet formation.

7. The apparatus of claim 6 in which the timing and control means is configured to start the drainage time measurement at the time of opening the dropleg valve means and conclude the measurement when the drainage time measurement means sense a decrease in surface reflectance in a newly formed sheet.

8. The apparatus of claim 1 in which the table means is a rotatable turntable having a plurality of angularly spaced apart sheet forming locations.

9. The apparatus of claim 8 in which the rotatable turntable has a sheet mold reservoir rinsing locaton positioned between each sheet forming location, said rinsing location being an unrestricted aperture through the turntable, said timing and control means enabling control of the turntable and sheet mold and dropleg positioning means to permit a thorough rinsing of the sheet mold reservoir between each sheet forming cycle.

10. The apparatus of claim 8 further including stepwise rotating means for rotating the turntable.

11. The apparatus of claim 1 in which the table means is a linearly movable table having a plurality of spaced apart sheet forming locations.

12. The apparatus of claim 11 in which the table means has at least one sheet mold rinsing location adjacent the sheet forming locations.

13. The apparatus of claim 12 which has a plurality of sheet forming locations and one sheet mold rinsing location and further including end-to-end fluid actuated cyclinder means to position the table means.

14. The apparatus of claim 11 further including fluid actuated cyclinder means to position the table means.

* * * * *